United States Patent

Rana et al.

[11] Patent Number: 5,843,995
[45] Date of Patent: Dec. 1, 1998

[54] INHIBITION OF HIV-1 REPLICATION USING OLIGOCARBAMATE DERIVATIVES

[75] Inventors: Tariq M. Rana, Piscataway; Ikramul Huq, Highland Park, both of N.J.

[73] Assignee: University of Medicine and Dentistry of New Jersey, New Brunswick, N.J.

[21] Appl. No.: 888,865

[22] Filed: Jul. 7, 1997

[51] Int. Cl.$^6$ .......................... A61K 31/24; C07C 205/16
[52] U.S. Cl. ............................................. 514/551; 560/24
[58] Field of Search ................................ 560/24; 514/551

[56] References Cited

PUBLICATIONS

Aboul–ela(1995), J. Mol. Biol., 253:313–32.
Calnan(1991), Genes Dev., 5:201–10.
Cullen(1992), Microbiol. Rev., 56:375–94.
Dintzis(1993), Proteins, 16:306–8.
Felber(1988), Science, 239;184–7.
Frankel(1988), Cell, 55:1189–94.
Hamy(1993), J. Mol. Biol., 230:111–23.
Jakobovits(1988), Mol. Cell Biol., 8:2555–61.
Milligan(1987), Nucl. Acids Res., 15:8783–98.
Milton(1992), Science, 256:1445–8.
Nordeen(1988). Biotechniques, 6:454–7.
Schumacher(1996). Science, 271:1854–7.
Stade(1989), Nucl. Acids Res., 17:9889–909.
Wang(1996), Biochemistry, 35:6491–9.
Wang(1996), J. Biol. Chem., 271:16995–8.
Zawadzke(1992), J. Am.Chem. Soc., 114:4002.
Zawadzke(1992), Proteins, 16:301–5.

*Primary Examiner*—Johann Richter
*Assistant Examiner*—Ebenezer Sackey
*Attorney, Agent, or Firm*—Klauber & Jackson

[57] ABSTRACT

Tat-inhibitory oligocarbamate derivatives of the formula I

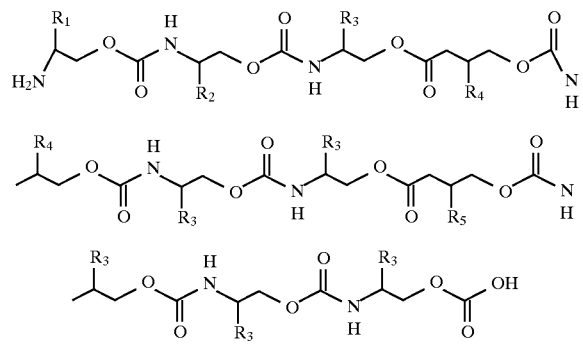

and analogs thereof, and the biologically and pharmaceutically acceptable salts thereof exhibit advantageous properties, including specific binding to TAR RNA with high affinities, and stability of the resultant oligocarbamate-RNA complexes to proteolytic digestion. Site-specific photocrosslinking experiments using a photoactive analog (4-thio-uracil) containing TAR RNA indicate that these oligocarbamates interact with RNA in the major groove. These oligocarbamates are thus capable of competing with the TAR RNA-binding domain of Tat protein and thus are useful as a therapeutic agents in the treatment of AIDS.

21 Claims, 5 Drawing Sheets

FIG. 1A

⁴⁷ Tyr-Gly-Arg-Lys-Lys-Arg-Arg-Gln-Arg-Arg-Arg ⁵⁷

RNA-binding Tat Peptide

FIG. 1B

Structure of Oligocarbamate Backbone

FIG. 1C

```
      G  G
    U    G34
   C    A
    C-G
    G-C
    G-C
    A-U
   UG-C
  C
23U
   A-U40
    G-C
    A-U
    C-G
    G-C
 17G-C45
``` wild-type TAR RNA

FIG. 1D

```
                 Strand 2
                     5'
              C-G
              C-G
              A-U
              C-G
           29C-G
              G-C
              A-U
             CG-C
            C
         23U
              A-U40
              G-C
              A-U
              C-G
           18C-G
              G-C
              C-G
              G-C
              G-C
           5'
         Strand 1
```

Duplex TAR RNA

FIG. 5B

INHIBITION OF HIV-1 REPLICATION USING OLIGOCARBAMATE DERIVATIVES

This work was supported in part by the National Institutes of Health Grants AI 34785, AI 01369, and TW00702. The government may have certain rights therein.

BACKGROUND OF THE INVENTION

RNA-protein interactions are important in many cellular functions, including transcription, RNA splicing, and translation. One example of such an interaction is the mechanism of trans-activation of the human immunodeficiency virus type 1 (HIV-1) gene expression that requires the interaction of Tat protein with the trans-activation responsive region (TAR) RNA, a 59-base stem-loop structure located at the 5'-end of all nascent HIV-1 transcripts.

The promoter of HIV-1, located in the U3 region of the viral long terminal repeat (LTR), is an inducible promoter which can be stimulated by the trans-activator protein, Tat. As in other lentiviruses, Tat protein is essential for trans-activation of viral gene expression.

Tat-derived peptides containing the arginine-rich RNA-binding domain of Tat are able to form in vitro complexes with TAR RNA. Structural studies of Tat protein show that the RNA-binding domain is not a rigid helix. Since the RNA-binding domain of Tat has a flexible structure, the symmetry of small peptides containing arginine-rich sequences may not be crucial in TAR RNA recognition.

In order to develop effective therapies for the treatment and prevention of AIDS, elucidation of the mechanisms by which it replicates in the human host is essential. Therefore, it is apparent that there still exists a need in the art for the identification and characterization of the agents which can prevent or retard the HIV-1 transcription process.

SUMMARY OF THE INVENTION

The present invention concerns oligocarbamate derivatives which can be utilized as peptide mimics for the recognition of, and binding by, RNA and DNA structures. More particularly, this invention relates to Tat-inhibitory oligocarbamate derivatives of the formula I wherein $R^1$ is a p-hydroxybenzyl or benzyl group;

$R^2$ is hydrogen or methyl;

$R^3$ is guanidinopropyl;

$R^4$ is aminobutyl or guanidino propyl; and $R^5$ is amidomethyl or amidoethyl; and analogs thereof, and the biologically and pharmaceutically acceptable salts thereof, which exhibit advantageous properties, including specific binding to HIV-1 TAR RNA with high affinities, and stability of the resultant oligocarbamate-RNA complexes to proteolytic digestion. Site-specific photocrosslinking experiments using a photoactive analog (4-thio-uracil) containing TAR RNA indicate that these oligocarbamates interact with RNA in the major groove. These oligocarbamates are thus capable of competing with the TAR RNA-binding domain of Tat protein. These compounds are thus useful in the treatment of HIV-1 infection by virtue of their ability to block the interaction of Tat protein with TAR RNA, thereby interfering with the transactivation step in the replication cycle of HIV-1. The rationale for this approach is that such oligocarbamates compete with the full length Tat protein for binding to TAR RNA, thereby preventing the required interactions between other domains in Tat protein and the nascent transcription apparatus.

It is an object of the present invention to provide compounds which are useful in the treatment of various pathologies, especially those such as HIV-1, by virtue of their ability to block the interaction of proteins and their RNA, especially Tat protein with TAR RNA, thereby interfering with the protein-RNA interaction, and in the case of HIV-1, with the transactivation step in the replication cycle of this virus.

It is further an object of this invention to provide pharmaceutical compositions suitable for the administration of such compounds.

It is a still further object of the present invention to provide a method of treating HIV-1 infection in mammals which comprises the administration of the compounds of the present invention.

Other objects and advantages will become apparent to those skilled in the art from a review of the ensuing description which proceeds with reference to the following illustrative drawings.

BRIEF DESCRIPTION OF THE DRAWING FIGURES

FIG. 1B is a schematic structure of the oligocarbamate backbone. The substituents of the sequence of the oligocarbamate correspond to the variant portions of the amino acids of the Tat peptide shown in FIG. 1A. The Tat-derived oligocarbamate was synthesized on an ABI 431 peptide synthesizer by using N-α-Fmoc-protected p-nitrophenyl carbonate monomers according to the methods described by Cho et al., Science 1993, 261, 1303–5. After cleavage from the resin, the oligocarbamate was purified by HPLC on a Zorbax 300 SB-C$_8$ column. The mass of fully deprotected and purified oligocarbamate was confirmed by FAB mass spectrometry; 1831.3 (M+H).

FIG. 1D shows the secondary structure of the designed duplex TAR RNA used in photocrosslinking experiments. Duplex RNA contains the nucleotides C18 to C29 and G36 to G44 from the wild-type TAR RNA sequence, and extra flanking base pairs to enhance hybridization of two RNA strands. Numbering of nucleotides in the duplex TAR RNA corresponds to their positions in wild-type TAR RNA. All RNAs were prepared by in vitro transcription. For transcription reactions (20 μL) containing 8.0 pmoles template DNA, 40–60 units of T7 polymerase (Promega) was used. For the synthesis of 4-thioU labeled RNA, UTP was replaced with 4-thioUTP (4 mM, final concentration) in the transcription buffer. 4-thio-UTP was synthesized according to the method of Stade et al. RNA purification and labeling were carried out as described in Bayer, P., et al. *J. Mol. Biol.* 247:529–535 (1995).

FIGS. 5A AND 5B are photographs showing the specificity of the oligocarbamate-TAR RNA crosslinking reaction determined by competition experiments. The oligocarbamate-RNA complexes were formed between 0.04 μM $^{32}$P-5'-end labeled duplex TAR RNA and 1.5 μM Tat-derived oligocarbamate in the presence of unlabeled wild-type TAR RNA (A) or mutant TAR RNA (B). (A): concentrations of the competitor RNA in lanes 1, 2, 3, 4, 5, and 6 were 0, 0.5, 1, 2, 3, and 4 μM, respectively. (B): concentrations of the competitor RNA in lanes 1, 2, 3, and 4 were 1, 2, 3, and 4 μM, respectively. Lane a; duplex RNA without UV. Lane b; duplex RNA with UV showing the electrophoretic mobility of RNA-RNA crosslink. Lane c; the oligocarbamate-RNA complex in the dark. The RNA-RNA and RNA-oligocarbamate crosslink are indicated by R-R and R-P XL, respectively.

DETAILED DESCRIPTION OF THE INVENTION

Protein-RNA and protein-DNA interactions are critical to the cellular replication process. Interruption of this process provides a method of interfering with the multiplication of many viral and bacterial pathogens, thereby providing therapeutic intervention in the progress of various diseases.

The Tat protein of human immunodeficiency virus type-1 (HIV-1) binds to its target RNA, TAR. and activates transcription. A 36-amino acid peptide portion, Tat(37–72). containing RNA-binding domain of Tat, binds specifically to TAR RNA.

The present invention provides by chemical synthesis oligocarbamate derivatives which are appropriately substituted to mimic the Tat(47–57) peptide.

The oligocarbamate derivatives of the present invention are represented by the following formula I wherein
  $R^1$ is a p-hydroxybenzyl or benzyl group;
  $R^2$ is hydrogen or methyl;
  $R^3$ is guanidinopropyl;
  $R^4$ is aminobutyl or guanidinopropyl; and
  $R^5$ is amidomethyl or amidoethyl; and analogs thereof, and the biologically and pharmaceutically acceptable salts thereof. Of these, certain derivatives are preferred, i.e., the derivatives wherein $R^5$ is an amidoethyl group. Especially preferred is the derivative wherein each of the variable R substituents is selected so as to mimic or simulate the naturally occurring Tat sequence as shown in SEQ ID NO:1. This derivative is thus a compound of formula I wherein $R^1$ is a p-hydroxybenzyl group, $R^2$ is hydrogen, $R^4$ is aminobutyl, and $R^5$ is amidoethyl group.

Surprisingly, it has been found that these oligocarbamates specifically bind TAR RNA with high affinities and interact with RNA in the widened major groove, as determined by electrophoretic mobility shift and site-specific photo-crosslinking experiments. The oligocarbamate derivatives inhibit the binding of the L peptide to TAR RNA in vitro, and thus inhibit the Tat trans-activation in vivo.

Such results demonstrate that the oligocarbamate derivatives of the present invention can recognize specific nucleic acid structures. Since these oligocarbamate derivative ligands are resistant to degradation by naturally occurring enzymes and do not induce a vigorous humoral immune response, they are thus useful to control protein-nucleic acid interactions in vivo.

To ascertain whether the oligocarbamate derivatives recognize naturally occurring nucleic acid structures, the Tat peptide (SEQ ID NO:1, FIG. 1) containing the basic-arginine rich region of Tat was synthesized by solid phase peptide synthesis methods. After HPLC purification and characterization by mass spectrometry, the Tat peptide was tested for TAR RNA binding. Similar to L-Tat, the oligocarbamate derivative was able to bind TAR RNA and failed to bind a mutant TAR RNA without the bulge residues.

Equilibrium dissociation constants of the oligocarbamate-TAR RNA complexes were measured using direct and competition electrophoretic mobility assays. Dissociation constants were calculated from multiple sets of experiments which showed that the oligocarbamate binds TAR RNA with a $K_d$ of 1.13 µM. To compare the RNA-binding affinities of the oligocarbamate to natural peptide, we synthesized a tat-derived peptide (Tyr47 to Arg57) containing the RNA-binding domain of Tat protein (FIG. 1). Dissociation constants of the Tat peptide-RNA complexes were determined from multiple sets of experiments under the same conditions used for oligocarbamate-TAR RNA complexes. These experiments showed that the Tat peptide (47–57) binds TAR RNA with a $K_d$ of 0.78 µM. A relative dissociation constant ($K_{rel}$) can be determined by measuring the ratios of wild-type Tat peptide to the oligocarbamate dissociation constants ($K_d$) for TAR RNA. Our results demonstrate that the calculated value for $K_{rel}$, was 0.69, indicating that the carbamate backbone structure did not significantly alter the TAR binding affinities of the unnatural biopolymer. Specificity of the oligocarbamate-TAR RNA complex formation was addressed by competition experiments. The oligocarbamate-RNA complex formation was inhibited by the addition of unlabeled wild-type TAR RNA and not by a mutant TAR RNA. These results indicate that the tat-derived oligocarbamate can specifically recognize TAR RNA.

While not wishing to be bound by any particular theory, there are a number of ways that the oligocarbamate derivative of formula I could interact with TAR RNA. Several lines of evidence suggest that Tat protein interacts with TAR RNA in a widened major groove.

Figure 1A:
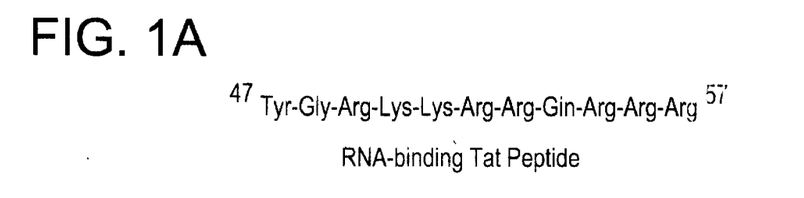
FIG. 1A is the sequence for the Tat-derived peptide, amino acids 47 to 57, containing the RNA-binding domain of Tat protein.
Figure 1B:
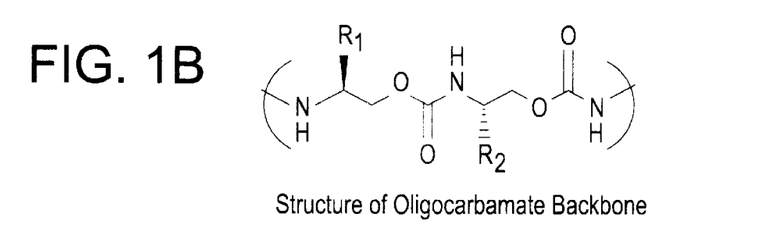
Figure 1C:
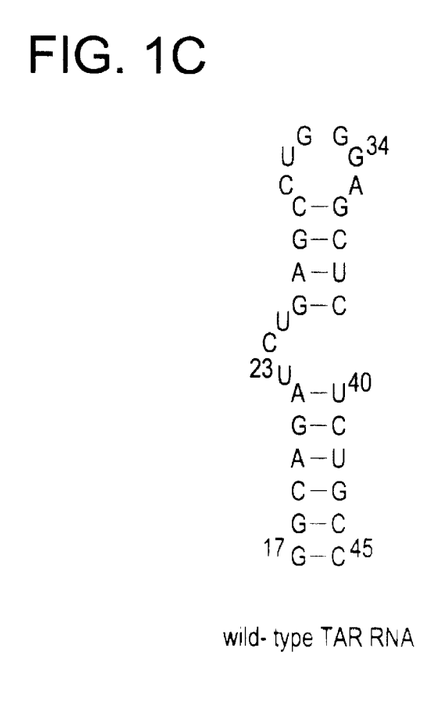
FIG. 1C shows the secondary structures of wild-type TAR RNA used in this study. Wild-type TAR RNA spans the minimal sequences that are required for Tat responsiveness in vivo and for in vitro binding of Tat-derived peptides. Wild-type TAR contains two non-wild-type base pairs to increase transcription by T7 RNA polymerase.
Figure 1D:
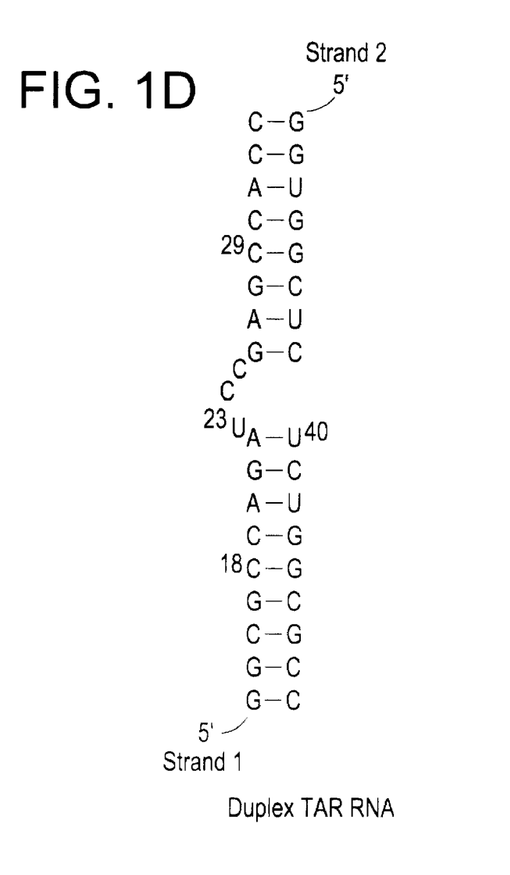
Figure 2:
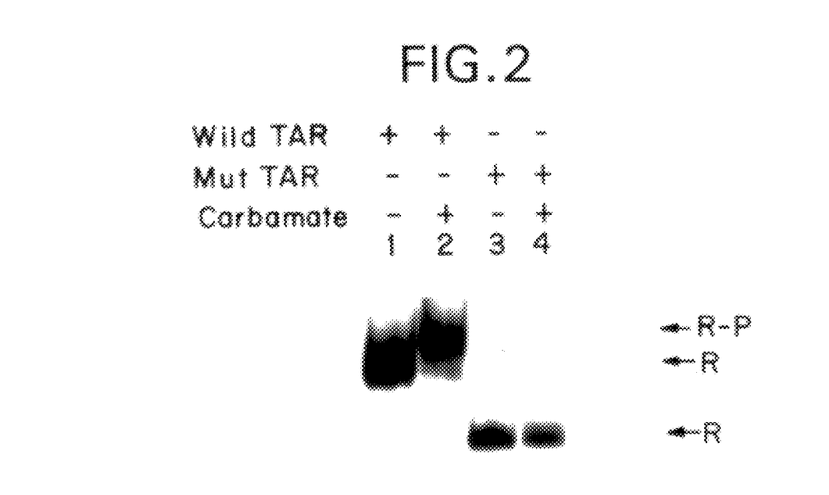
FIG. 2 is a photograph showing the electrophoretic mobility shift analysis for the Tat-derived oligocarbamate binding to wild-type (wild) and trinucleotide bulge mutant (mut) TAR RNA. RNA and RNA-oligocarbamate complexes are indicated as R and R-P, respectively. $^{32}$P-5'-end labeled TAR RNAs were heated to 85° C. for 3 minutes and then cooled to room temperature in TK buffer (50 mM Tris-HCl (pH 7.4), 20 mM KCl, 0.1% Triton X-100). The oligocarbamate was added alone or along with the competitor RNAs (wild-type TAR or mutant TAR) pre-heated in TK buffer at 85° C. for 3 minutes and cooled to room temperature. The oligocarbamate-RNA binding reactions were carried out at room temperature for 1 hour and stopped by adding 30% glycerol. The oligocarbamate-RNA complexes were resolved on a non-denaturing 12% acrylamide gel and visualized by autoradiography or Phosphorimaging.
Figure 3:
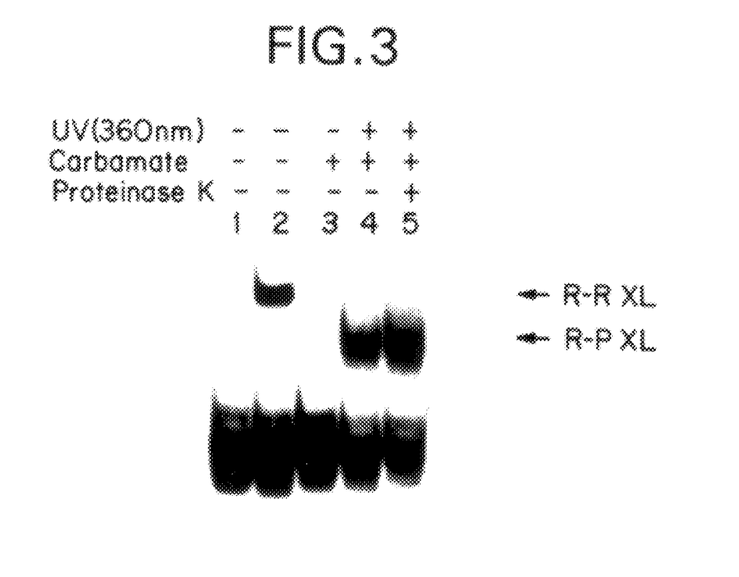
FIG. 3 is a photograph showing the site-specific photo-crosslinking reaction of TAR RNA duplex labeled with 4-thioUracil at position 23 with the oligocarbamate. The RNA-RNA and RNA-oligocarbamate crosslink are indicated by R-R and R-P XL, respectively. For photochemical reactions, RNA duplex was prepared by hybridizing two strands. Strand 1 of the duplex was 5'-end labeled with $^{32}$P. Preformed RNA duplexes (0.04 μM) in the absence or presence of the oligocarbamate (1.5 μM) were irradiated (360 nm) and analyzed by denaturing gels as described in Wang et al., *Biochemistry,* 1996 35:6491–6499.
Figure 4A:
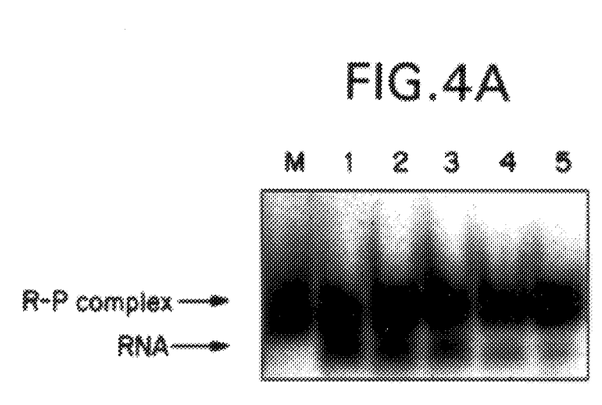
FIG. 4A is a photograph showing the specificity of the oligocarbamate-TAR complex formation determined by competition assays. RNA-oligocarbamate complexes were formed between 0.04 μM $^{32}$P-5'-end labeled TAR RNA and 1.5 μM of the Tat-derived oligocarbamate in the presence of unlabeled trinucleotide bulge mutant TAR RNA (A) or wild-type TAR RNA
Figure 4B:
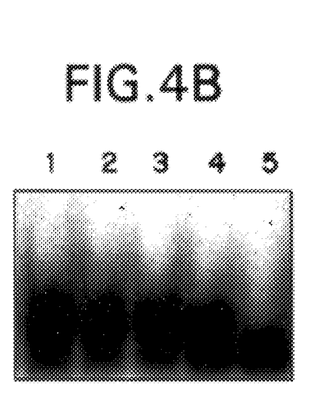
FIG. 4B is a photograph showing the concentrations of the competitor RNA in lanes 1, 2, 3, 4, 5 were 0.5, 1, 2, 3, and 4 μM, respectively. Lane M is a marker lane showing the RNA and the RNA-oligocarbamate complexes are indicated as R-P.

A site-specific crosslinking method based on 4-thio-uracil (4-thioU) photochemistry was used to determine the conformation of TAR RNA and its interaction with Tat protein under physiological conditions. To probe the oligocarbamate derivative-RNA interactions, TAR RNA containing 4-thioU at position 23 was synthesized and photocrosslinking experiments were performed as shown in FIG. 3. Irradiation of the oligocarbamate derivative-RNA complex yields a new band with electrophoretic mobility less than that of the RNA (FIG. 3, lane 4). Both the oligocarbamate derivative and UV (360 nm) irradiation are required for the formation of this crosslinked RNA-peptide complex (see lanes 3 and 4). Since the crosslinked oligocarbamate derivative-RNA complex is stable to alkaline pH (9.5), high temperature (85° C.) and denaturing conditions (8M urea, 2% SDS), it can be concluded that a covalent bond is formed between TAR RNA and the peptide during the crosslinking reaction.

To test the protease stability of the oligocarbamate derivative-RNA complexes, the oligocarbamate derivative-RNA crosslink products were subjected to very vigorous proteinase K digestion which showed that the complexes were completely stable and there were no signs of oligocarbamate derivative degradation (lane 5). Under similar proteinase K treatment, Tat-TAR photocrosslink products resulted in a complete loss of RNA-protein crosslinking and a gain in free RNA as observed by band intensities on the gel.

Figure 5A:
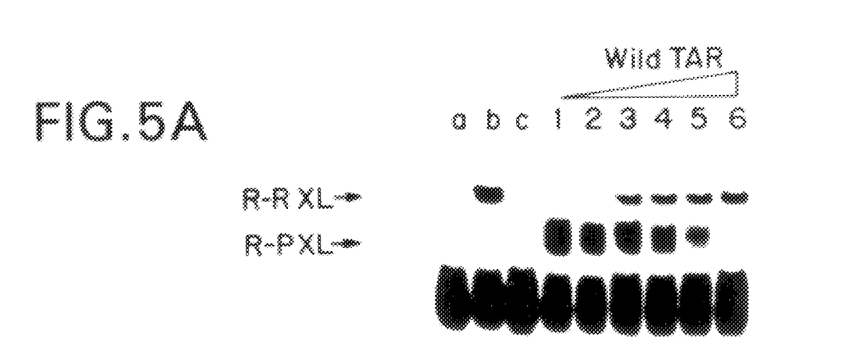
Figure 5B:
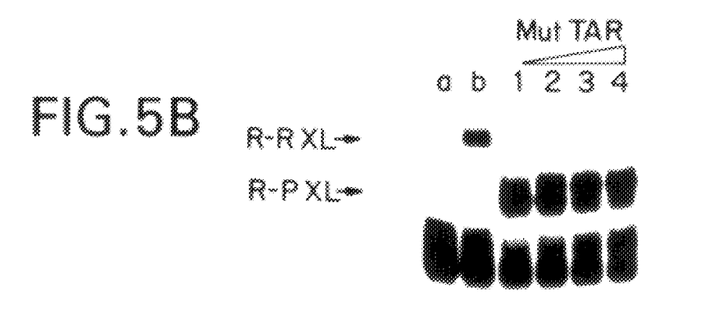

The specificity of the crosslinking reaction was established by competition experiments. Crosslinking was inhibited by the addition of unlabeled wild-type TAR RNA and not by a mutant TAR RNA lacking the trinucleotide bulge (FIGS. 5A and 5B). Therefore, it can be concluded that formation of a specific RNA-protein complex between TAR RNA and a Tat-similar oligocarbamate derivative is necessary for photocrosslinking. As the amount of wild-type competitor RNA was increased, a decrease in RNA-protein crosslink was observed (as expected), however, an increase in RNA-RNA crosslink was also observed. These results indicate that interstrand RNA crosslink is inhibited by the presence of the RNA-binding oligocarbamate ligand. A similar result was previously obtained in photocrosslinking experiments employing a 34 amino acid L-Tat fragment and 4-thio-U containing TAR RNA.

To determine whether the oligocarbamate derivative can inhibit Tat-TAR complex formation in vitro, photocrosslinking experiments of the Tat-TAR complex were carried out in the presence of increasing amounts of the oligocarbamate derivative followed by proteinase K digestion. An RNA-protein crosslink was observed in L-Tat-TAR complex which was degraded to smaller RNA-peptide complexes by the addition of proteinase K enzyme. Since D-Tat-TAR crosslink is resistant to proteolysis, increasing the amount of the oligocarbamate derivative prior to the crosslinking reactions resulted in an increase in RNA-protein crosslink after proteinase K digestion. A decrease in smaller RNA-peptide crosslink products was also observed as the concentration of the oligocarbamate derivative was increased. These results demonstrate that the oligocarbamate derivative of formula I can compete with Tat to form a complex with TAR RNA in vitro.

To determine if the oligocarbamate derivative inhibits Tat transactivation in vivo, oligocarbamate derivative with pSV2-Tat and pAL plasmids was crossfected into HeLa cells containing an integrated LTR-CAT reporter. Plasmids pSV2Tat and pAL express first exon of Tat protein and luciferase enzyme, respectively. Transfection of pSV2Tat enhanced transcription as determined by CAT activity. Increasing the amount of the oligocarbamate derivative results in a decrease of CAT activity while luciferase activity was not affected. Tat trans-activation was inhibited more than 50% by 5 µg oligocarbamate derivative. Transfection of Tat peptides did not decrease CAT activity suggesting that L-peptides are not stable to proteolysis in vivo. Such results indicate that the oligocarbamate derivative specifically inhibits trans-activation by Tat protein.

These findings indicate that simulated-Tat oligocarbamate derivatives of the present invention bind TAR RNA specifically and interact in the widened major groove of TAR RNA in a similar fashion to that observed for Tat. These findings show that a small tat-derived oligocarbamate binds TAR RNA specifically and interacts in the widened major groove of TAR RNA. Due to the difference in backbone structure, oligocarbamates may differ from peptides in hydrogen-bonding properties, lipophilicity, stability, and conformational flexibility. Moreover, oligocarbamates are resistant to proteinase K degradation. These characteristics of oligocarbamates may be useful in improving pharmacokinetic properties relative to peptides. RNA recognition by an unnatural biopolymer provides a new approach for the design of drugs which will modulate RNA-protein interactions.

The utility of the oligocarbamate derivatives of formula I is further demonstrated by their ability to inhibit replication of HIV-1 in an acute infection assay.

A similar approach has been reported using the cationic peptide, N-acetyl-(DArg)$_9$-NH$_2$. Antiviral activity of that peptide, however, was found to be via inhibition of viral entry, consistent with antiviral activity being observed when the cells were pretreated with peptide 24 hours prior to infection. In that study, the possibility of inhibition of transactivation by blocking Tat protein was suggested, but not proven, and no evidence of the peptide displaying specificity for TAR RNA was presented.

The instant invention thus provides a method of treating a retroviral protease infection in a mammal in need of such treatment. More particularly, the oligocarbamates of the present invention can be utilized as Tat protein RNA-binding domain mimics to treat the HIV-1 infection, and the resultant AIDS. The mammal under treatment can be a human, monkey, cat or the like, with the treatment of humans being particularly preferred. A Tat antagonist would also be useful for ameliorating the pathogenic effects of Tat protein on host cells due to interactions with TAR-like elements on cellular transcripts. Recent studies on peptide analogs of the core domain sequence of Tat protein, which is believed to interact with host cell factors rather than with virally encoded RNA, have lead to the same suggestion for a new class of therapeutic agents for AIDS based on inhibition of the transactivation step in the HIV-1 replication cycle.

The oligocarbamate derivatives of formula I and their analogs can be synthesized by conventional solution methods, or by solid phase synthetic techniques known in the art.

Throughout the specification and appended claims, the oligocarbamate derivatives of formula I, and its analogs and salts, encompass all stereo, optical and geometrical isomers thereof where such isomers exist, as well as the pharmaceutically acceptable salts and solvates thereof. Where appropriate, the oligocarbamate derivative or its analogs can be utilized as its corresponding amide form.

The term "biologically and pharmaceutically acceptable salts" is intended to include any such salt derived from an inorganic or organic acid which is tolerated by the mammalian system. These salts include, but are not limited to, acetate, adipate, alginate, citrate, aspartate, benzoate, benzenesulfonate, bisulfate, hexanoate, succinate, fumarate, hydrochloride, hydrobromide, lactate, maleate, phosphate, sulfate, methanesulfonate, oxalate, propionate, tosylate, and mesylate. Examples of acids which can be used to form such salts include such inorganic acids as hydrochloric acid, sulfuric acid and phosphoric acid, and such organic acids such as oxalic acid, maleic acid, succinic acid and citric acid.

The nomenclature used to define the oligocarbamates is in accordance with conventional polypeptide representation wherein the amino group at the N-terminal appears to the left and the carboxyl group at the C-terminal to the right. $NH_2$ refers to the free amino group present at the amino terminus of the oligocarbamate. COOH refers to the free carboxy group present at the carboxy terminus of the oligocarbamate.

Accordingly, oligocarbamate derivative analogs displaying substantially equivalent activity to the derivatives of formula I are likewise contemplated for use in the present invention. These modifications can be obtained through synthesis utilizing the appropriate starting material.

Also, the term "active agent," "active ingredient" and "active medicament" are intended to include within their scope the oligocarbamate derivative of formula I specifically recited herein as well as all substantially homologous analogs thereof.

In keeping with standard polypeptide nomenclature, *J. Biol. Chem.*, 243:3552–59 (1969), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |

-continued

| TABLE OF CORRESPONDENCE | | |
|---|---|---|
| SYMBOL | | |
| 1-Letter | 3-Letter | AMINO ACID |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A substituent on the carbamate backbone in the oligocarbamate derivative of this invention can be changed from the corresponding substituent of the amino acid in the naturally occurring Tat-peptide sequence in a non-conservative manner (i.e., by changing a substituent of the starting carbonates belonging to a grouping of carbonates having a particular size or characteristic to a carbamate belonging to another grouping) or in a conservative manner (i.e., by changing a carbonate belonging to a grouping of carbonates having a particular size or characteristic to a carbonate belonging to the same grouping). Such a conservative change generally leads to less change in the structure and function of the resulting oligocarbonate. The present invention should be considered to include analogs whose sequences contain conservative changes which do not significantly alter the activity or binding characteristics of the resulting oligocarbonate.

The following is one example of various groupings of carbonates which have the formula wherein R is a substituent found in a naturally occurring amino acid.

| Carbonates with nonpolar R groups | |
|---|---|
| R | |
| $CH_3$ | (methyl, Alanine analog) |
| $CH_3-CH(CH_3)-$ | (isopropyl, Valine analog) |
| $CH_3-CH(CH_3)-CH_2-$ | (isobutyl, Leucine analog) |
| $CH_3-CH_2-CH(CH_3)-$ | (1-methylpropyl, Isoleucine analog) |
| $\phi CH_2-$ | (benzyl Phenylalanine analog) |
| $CH_3-S-CH_2-CH_2-$ | (methylthioethyl, Methionine analog) |

-continued

Carbonates with uncharged polar R groups

| R | |
|---|---|
| H | (hydrogen, Glycine analog) |
| HO—CH$_2$— | (hydroxymethyl, Serine analog) |
| CH$_3$—CH(OH)— | (α-hydroxyethyl, Threonine analog) |
| HS—CH$_2$— | (thiomethyl, Cysteine analog) |
| HO-φ-CH$_2$— | (hydroxybenzyl, Tyrosine analog) |
| $\underset{H_2N-C-CH_2-}{\overset{O}{\parallel}}$ | (amidomethyl, Asparagine analog) |
| $\underset{H_2N-C-CH_2-CH_2-}{\overset{O}{\parallel}}$ | (amidoethyl, Glutamine analog) |

Carbonates with charge polar R groups

| | |
|---|---|
| HOOC—CH$_2$— | (carboxymethyl, Aspartic acid analog) |
| HOOC—CH$_2$—CH$_2$— | (carboxyethyl, Glutamic acid analog) |

Basic carbonates

| | |
|---|---|
| H$_2$N—(CH$_2$)$_4$— | (aminobutyl, Lysine analog) |
| $\underset{H_2N-C-NH-CH_2-CH_2-CH_2-}{\overset{NH_2}{\parallel}}$ | (guanidinopropyl, Arginine analog) |

Another grouping may be those carbonates with phenyl groups, such as the phenylalanine and tyrosine analogs.

Another grouping may be according to molecular weight (i.e., size of R groups), with groups of similar weight being replaceable by other groups of similar weight.

Particularly preferred substitutions are the glutamine analog for the arginine analog or lysine analog.

Carbonate substitutions may also be introduced to substitute a carbonate with a particularly preferable property. For example, a cysteine analog may be introduced as a potential site for a disulfide bridge with another cysteine analog.

Representative analogs of the oligocarbonate of formula I thus include those wherein $R^1$ is p-hydroxybenzyl;
$R_2$ is hydrogen;
$R^4$ is aminobutyl; and
$R^5$ is amidoethyl;
$R^1$ is benzyl;
$R^2$ is hydrogen;
$R^4$ is aminobutyl; and
$R^5$ is amidoethyl;
$R^1$ is P-hydroxybenzyl;
$R^2$ is hydrogen;
$R^1$ is P-hydroxybenzyl;
$R^2$ is hydrogen;
$R^4$ is amidobutyl; and
$R^5$ is amidomethyl.

The active oligocarbonate derivative for use in the present invention can be, and is preferably, administered as a medicament, i.e., a pharmaceutical composition. As discussed earlier, the oligocarbamate derivatives and their analogs of the present invention, may be prepared in pharmaceutical compositions, with a suitable carrier and at a strength effective for administration by various means to a patient experiencing an adverse medical condition associated with specific neuronal degeneration for the treatment thereof. A variety of administrative techniques may be utilized, among them parenteral techniques such as subcutaneous, intravenous and intraperitoneal injections, catheterizations and the like. Average quantities of the polypeptide or its analogs may vary and in particular should be based upon the recommendations and prescription of a qualified physician.

The pharmaceutical compositions used in the methods of this invention for administration to animals and humans comprise the active compound in combination with a pharmaceutical carrier or excipient.

The medicament can be in the form of tablets (including lozenges and granules), dragees, capsules, pills, ampoules, intranasal sprays, or suppositories comprising the compound of the invention.

"Medicament" as used herein means physically discrete coherent portions suitable for medical administration. "Medicament in dosage unit form" as used herein means physically discrete coherent units suitable for medical administration, each containing a daily dose or a multiple (up to four times) or a sub-multiple (down to a fortieth) of a daily dose of the active compound of the invention in association with a carrier and/or enclosed within an envelope. Whether the medicament contains a daily dose, or, for example, a half, a third or a quarter of a daily dose will depend on whether the medicament is to be administered once, or, for example, twice three times or four times a day, respectively.

Advantageously, the compositions are formulated as dosage units, each unit being adapted to supply a fixed dose of active ingredients. Tablets, coated tablets, capsules, ampoules, intranasal sprays and suppositories are examples of preferred dosage forms according to the invention. It is only necessary that the active ingredient constitute an effective amount, i.e., such that a suitable effective dosage will be consistent with the dosage form employed in single or multiple unit doses. The exact individual dosages, as well as daily dosages, will, of course, be determined according to standard medical principles under the direction of a physician.

The active compound can also be administered as suspensions, solutions and emulsions of the active compound in aqueous or non-aqueous diluents, syrups, granulates or powders.

Diluents that can be used in pharmaceutical compositions (e.g., granulates) containing the active compound adapted to be formed into tablets, dragees, capsules and pills include the following: (a) fillers and extenders, e.g., starch, sugars, mannitol and silicic acid; (b) binding agents, e.g., carboxymethyl cellulose and other cellulose derivatives, alginates, gelatine and polyvinyl pyrrolidone; (c) moisturizing agents, e.g., glycerol; (d) disintegrating agents, e.g., agar-agar, calcium carbonate and sodium bicarbonate; (e) agents for retarding dissolution, e.g., paraffin; (f) resorption accelerators, e.g., quaternary ammonium compounds; (g) surface active agents, e.g., cetyl alcohol, glycerol monostearate; (h) adsorptive carriers, e.g., kaolin and bentonite; (i) lubricants, e.g., talc, calcium and magnesium stearate and solid polyethylene glycols.

The tablets, dragees, capsules and pills comprising the active compound can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, from polymeric substances or waxes.

The active ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g., cocoa oil and high esters, (e.g., $C_{14}$-alcohol with $C_{16}$-fatty acid]) or mixtures of these diluents.

The pharmaceutical compositions which are solutions and emulsions can, for example, contain the customary diluents (with, of course, the above-mentioned exclusion of solvents having a molecular weight below 200, except in the presence of a surface-active agent), such as solvents, dissolving agents and emulsifiers. Specific non-limiting examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example, ground nut oil, glycerol, tetrahydrofurfuryl alcohol, polyethylene glycols and fatty acid esters of sorbitol or mixtures thereof.

For parenteral and intranasal administration, solutions and suspensions should be sterile, e.g., water or arachis oil contained in ampoules and, if appropriate, blood-isotonic.

The pharmaceutical compositions which are suspensions can contain the usual diluents, such as liquid diluents, e.g., water, ethyl alcohol, propylene glycol, surface active agents (e.g., ethoxylated isostearyl alcohols, polyoxyethylene sorbitols and sorbitan esters), microcrystalline cellulose, aluminum methahydroxide, bentonite, agar-agar and tragacanth, or mixtures thereof.

The pharmaceutical compositions can also contain coloring agents and preservatives, as well as perfumes and flavoring additions (e.g., peppermint oil and eucalyptus oil, and sweetening agents, (e.g., saccharin and aspartame).

The pharmaceutical compositions will generally contain from 0.5 to 90% of the active ingredient by weight of the total composition.

In addition to the active compound, the pharmaceutical compositions and medicaments can also contain other pharmaceutically active compounds.

Any diluent in the medicaments of the present invention may be any of those mentioned above in relation to the pharmaceutical compositions. Such medicaments may include solvents of molecular weight less than 200 as the sole diluent.

It is envisaged that this active compound will be administered perorally, intranasally, parenterally (for example, intramuscularly, intrathecally, intraperitoneally, subcutaneously, transdermally or intravenously), rectally or locally, preferably intranasally or parenterally, especially perlingually, or intravenously. Most preferably, the peptide of formula I, or its analog or salt, is administered by the intranasal or intravenous route.

The dosage rate, is preferably in the range of 0.01 to 20 mg/kg of body weight, and most preferably in the range of 0.5 to 5 mg/kg of body weight, and will be a function of the nature and body weight of the subject to be treated, the individual reaction of this subject to the treatment, type of formulation in which the active ingredient is administered, the mode in which the administration is carried out and the point in the progress of the disease or interval at which it is to be administered. Thus, it may in some case suffice to use less than a minimum dosage rate, while other cases an upper limit must be exceeded to achieve the desired results. Where larger amounts are administered, it may be advisable to divide these into several individual administrations over the course of the day. In this regard, the intranasal administration may utilize metered dose devices known in the art.

The following examples are presented in order to more fully illustrate the preferred embodiments of the invention. They should in no way be construed, however, as limiting the broad scope of the invention. The following examples are presented in order to more fully illustrate the preferred embodiments of the invention. They should in no way be construed, however, as limiting the broad scope of the invention.

EXAMPLES

Example 1

METHODS

RNA and Tat-derived peptide synthesis

All RNAs were prepared by in vitro transcription [29]. For transcription reactions (20 μL) containing 8.0 pmoles template DNA, 40–60 units of T7 polymerase (Promega) was used. For the synthesis of 4-thioU labeled RNA, UTP was replaced with 4-thioUTP (4 mM, final concentration) in the transcription buffer. 4-thio-UTP was synthesized according to the method of Stade, K., Rinke-Appel, J. & Brimacombe, R. *Nucl. Acids Res.* 17:9889–9909(1989). RNA purification and labeling were carried out as described in Wang et al., *Biochemistry* 35, 6491–6499 (1996).

Tat-derived peptides were synthesized on an ABI 431 peptide synthesizer by using N-α-Fmoc-protected monomers [24]. After cleavage from the resin, the peptides were purified by HPLC on a Zorbax 300 SB-$C_8$ column. The mass of fully deprotected and purified peptide was confirmed by FAB mass spectrometry; 4186.8 (M+H).

Gel-Shift Assays $^{32}$P-5'-end labeled TAR RNAs were heated to 85° C. for 3 minutes and then cooled to room temperature in TK buffer (50 mM Tris-HCl (pH 7.4), 20 mM KCl, 0.1% Triton X-100). The Tat peptide was added alone or along with the competitor RNAs (wild-type TAR or mutant TAR) preheated in TK buffer at 85° C. for 3 minutes and cooled to room temperature. The peptide-RNA binding reactions were carried out at room temperature for 1 hour and stopped by adding 30% glycerol. The peptide-RNA complexes were resolved on a non-denaturing 12% acrylamide gel and visualized by autoradiography or Phosphorimaging.

Site-Specific Photo-Cross-Linking Reactions

For photochemical reactions, RNA duplex was prepared by hybridizing two strands [24]. Strand 1 of the duplex was 5'-end labeled with $^{32}$P. Preformed RNA duplexes (0.02 μM) in the absence or presence of the peptide (0.1 μM) were irradiated (360 nm) and analyzed by denaturing gels as described in Wang et al., *Biochemistry* 35, 6491–6499 (1996).

While the invention has been described and illustrated herein by references to various specific material, procedures and examples, it is understood that the invention is not restricted to the particular material combinations of material, and procedures selected for that purpose. Numerous variations of such details can be implied as will be appreciated by those skilled in the art.

The following is a list of documents related to the above disclosure and particularly to the experimental procedures and discussions. The documents should be considered as incorporated by reference in their entirety.

Cullen, B. R. *Microbiol. Rev.* 56:375–394 (1992).
Milton, R. C., Milton, S. C. & Kent, S. B. *Science* 256:1445–8 (1992).
Zawadzke, L. E. & Berg, J. M. *J. Am. Chem. Soc.* 114:4002 (1992).
Zawadzke, L. E. & Berg, J. M. *Proteins* 16:301–5 (1993).
Schumacher, T. N. M., et al. *Science* 271:1854–1857 (1996).
Dintzis, H. M., Symer, D. E., Dintzis, R. Z., Zawadzke, L. E. & Berg, J. M. *Proteins* 16:306–8 (1993).

Hamy, F., et al. *J. Mol. Biol.* 230:111–123 (1993).
Wang, Z. & Rana, T. M. *Biochemistry* 35:6491–6499 (1996).
Wang, Z., Wang, X. & Rana, T. M. *J. Biol. Chem.* 271:16995–16998 (1996).
Frankel, A. D. & Pabo, C. O. *Cell* 55:1189–1194 (1988).
Nordeen, S. K. *Biotechniques* 6:454–457 (1988).
Felber, B. K. & Pavlakis, G. N. *Science* 239:184–187 (1988).
Milligan, J. F., Groebe, D. R., Witherell, G. W. & Uhlenbeck, O. C. *Nucl. Acids Res.* 15:8783–8798 (1987).
Jakobovits, A., Smith, D. H., Jakobovits, E. B. & Capon, D. J. *Mol. Cell. Biol.* 8:2555–2561 (1988).
Aboul-ela, F., Karn, J. & Varani, G. *J. Mol. Biol.* 253:313–332 (1995).
Calnan, B. J.; Biancalana, S.; Hudson, D.; Frankel, A. D. *Genes Dev.* 1991, 5, 201–210.
Wang, Z.; Wang, X.; Rana, T. M. *J. Biol. Chem.* 1996, 271, 16995–16998.
Jakobovits, A.; Smith, D. H.; Jakobovits, E. B.; Capon, D. J. *Mol. Cell. Biol.* 1988, 8, 2555–2561.
Milligan, J. F.; Groebe, D. R.; Witherell, G. W.; Uhlenbeck, O. C. *Nucl. Acids Res.* 1987, 15, 8783–8798.
Stade, K.; Rinke-Appel, J.; Brimacombe, R. *Nucl. Acids Res.* 1989, 17, 9889–9909.

What is claimed is:

1. An oligocarbamate derivative of the formula wherein $R^1$ is a p-hydroxybenzyl or benzyl group;

$R^2$ is hydrogen or methyl;

$R^3$ is guanidinopropyl;

$R^4$ is aminobutyl or guanidino propyl; and $R^5$ is amidomethyl or amidoethyl; and analogs thereof, and the biologically and pharmaceutically acceptable salts thereof.

2. The derivative of claim 1 wherein the C-terminal residue contains an amide group.

3. The derivative of claim 1 wherein $R^1$ is a p-hydroxybenzyl group.

4. The derivative of claim 1 wherein $R^2$ is hydrogen.

5. The derivative of claim 1 wherein $R^4$ is aminobutyl.

6. The derivative of claim 1 wherein $R^5$ is amidoethyl.

7. The derivative of claim 1 wherein $R^1$ is a p-hydroxybenzyl group, $R^2$ is hydrogen, $R^4$ is aminobutyl, and $R^5$ is amidoethyl.

8. A pharmaceutical composition comprising an oligocarbamate of the formula wherein $R^1$ is a p-hydroxybenzyl or benzyl group;

$R^2$ is hydrogen or methyl;

$R^3$ is guanidinopropyl;

$R^4$ is aminobutyl or guanidino propyl; and $R^5$ is amidomethyl or amidoethyl;

or an analog thereof, or a biologically and pharmaceutically acceptable salt thereof, and a pharmaceutically acceptable carrier therefor.

9. The composition of claim 8 wherein the C-terminal residue contains an amide group.

10. The composition of claim 8 wherein $R^1$ is a p-hydroxybenzyl group.

11. The composition of claim 8 wherein $R^2$ is hydrogen.

12. The composition of claim 8 wherein $R^4$ is aminobutyl.

13. The composition of claim 8 wherein $R^5$ is amidoethyl.

14. The composition of claim 8 wherein $R^1$ is a p-hydroxybenzyl group, $R^2$ is hydrogen, $R^4$ is aminobutyl, and $R^5$ is amidoethyl.

15. A method of inhibiting HIV-1 replication which comprises administration of an oligocarbamate of the formula wherein $R^1$ is a p-hydroxybenzyl or benzyl group;

$R^2$ is hydrogen or methyl;

$R^3$ is guanidinopropyl;

$R^4$ is aminobutyl or guanidino propyl; and $R^5$ is amidomethyl or amidoethyl; or an analog thereof, or a biologically and pharmaceutically acceptable salt thereof.

16. The method of claim 15 wherein the C-terminal residue contains an amide group.

17. The method of claim 15 wherein $R^1$ is a p-hydroxybenzyl group.

18. The method of claim 15 wherein $R^2$ is hydrogen.

19. The method of claim 15 wherein $R^4$ is aminobutyl.

20. The method of claim 15 wherein $R^5$ is amidoethyl.

21. The method of claim 15 wherein $R^1$ is a p-hydroxybenzyl group, $R^2$ is hydrogen, $R^4$ is aminobutyl, and $R^5$ is amidoethyl.

* * * * *